United States Patent [19]

Lamparsky

[11] 4,278,817
[45] Jul. 14, 1981

[54] NOVEL PRENYL 4-CARANONES

[75] Inventor: Dietmar Lamparsky, Wangen, Switzerland

[73] Assignee: Givaudan Corporation, Clifton, N.J.

[21] Appl. No.: 96,721

[22] Filed: Nov. 21, 1979

[30] Foreign Application Priority Data

Dec. 5, 1978 [CH] Switzerland ............... 12390/78

[51] Int. Cl.$^3$ .................... C07C 49/417; C07C 49/29
[52] U.S. Cl. ......................................................... 568/374
[58] Field of Search ............... 252/522; 568/375, 374, 568/376

[56] References Cited

U.S. PATENT DOCUMENTS 3,686,097  8/1972  Kropp ........................... 568/374

OTHER PUBLICATIONS

Cocker et al., "J. Chem. Soc." (c) 1967, p. 485.
Cocker et al., Tet. Letters, 1966, (13) p. 1409.
Teisseire et al., "Recherches", No. 16, p. 119 (1967).
Brown et al., "J. Amer. Chem. Soc.", 89, p. 1933.

*Primary Examiner*—Werren B. Lone
*Attorney, Agent, or Firm*—Robert F. Tavares; Thomas Cifelli, Jr.

[57] ABSTRACT

Novel prenyl 4-caranones of the general formula:

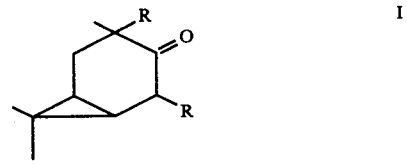

I wherein:
one R group represents a 3-methyl-2-butenyl group and
the other a hydrogen atom are useful olfactory agents in the preparation of fragrance materials.

5 Claims, No Drawings

NOVEL PRENYL 4-CARANONES

The present invention is concerned with novel odorant substances.

The novel odorant substances provided by the present invention are compounds of the general formula

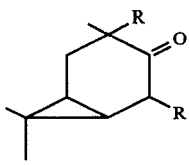

wherein one of the R symbols represents the 3-methyl-2-butenyl group and the other represents a hydrogen atom.

The foregoing is accordingly intended to embrace 3,7,7-trimethyl-3-(3'-methyl-2'-butenyl)-bicyclo[4.1.0]-heptan-4-one of formula Ia and 3,7,7-trimethyl-5-(3'-methyl-2'-butenyl)-bicyclo[4.1.0]-heptan-4-one of formula Ib

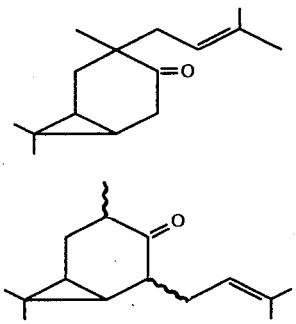

as well as all diastereoisomers of Ia and Ib which are feasible having regard to the substituents on the six-membered ring.

The invention is also concerned with a process for the manufacture of the compounds of formula I.

This process comprises reacting 4-caranone of the formula

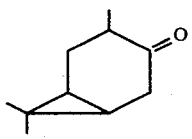

with a prenyl halide.

Cis-4-caranone is preferably used as the starting material of formula II.

Any prenyl halide can be used in the present process, but prenyl chloride is preferred.

The reaction is preferably carried out in the presence of a strong inorganic base such as an alkali metal hydroxide (e.g. potassium hydroxide), an alkaline earth metal hydroxide (e.g. calcium hydroxide), an alkali metal amide (e.g. sodamide) or an alkali metal hydride (e.g. sodium hydride). However, the reaction can also be carried out in the presence of an organic base such as, for example, potassium tert.butoxide.

The reaction can be carried out in the presence or absence of a solvent. Especially suitable solvents are aprotic or slightly polar solvents (e.g. dimethoxymethane, dimethoxyethane, diethyl ether or tertrahydrofuran).

The reaction temperature conveniently lies between approximately $-20°$ C. and $+50°$ C., preferably between $0°$ C. and $20°$ C. Lower temperatures are industrially unpractical, while higher temperatures can readily lead to an undesired two-fold prenylation of the cis-4-caranone.

According to the process provided by the present invention there is obtained an isomer mixture of Ia and Ib, usually in the ratio of about 80–90% of Ia and 20–10% of Ib.

Where desired, the separation of the isomer mixture (in which Ia predominates) can be carried out in the customary manner, for example, by means of column chromatography or preparative gas chromatography. As will be evident from the following, the organoleptic properties of the isomers of I do not differ fundamentally so that it is preferred, on economical ground especially, to use the isomer mixture.

On the basis of their organoleptic properties, the compounds of formula I are excellently suited as odorant substances and this invention is concerned with their use as odorant substances.

The compounds of formula I, especially the compound of formula Ia, are characterized by an interesting green note, which hitherto was absent from the palette of the perfumer, in that they combine together in one compound at the same time facets of the flowery, fatty, herby and woody direction and, moreover, display a long-lasting action in compositions. The evaluation of the olfactory properties of the individual components isolated from the mixture of I indicates that the odoriferous individuality of the ketone mixture I in accordance with the invention is due predominantly to the compound Ia, although the isomers of formula Ib are not substantially different from Ia in their olfactory notes and, in particular, are without any disturbing effect on the overall odour.

A separation of the isomer mixture is therefore, as mentioned earlier, uneconomical, and the mixture Ia/Ib obtainable in accordance with the invention can advantageously be used as such for the manufacture of odorant compositions.

Thus, I combines with numerous known natural or synthetic ingredients of odorant compositions, whereby the range of natural ingredients can embrace not only readily-volatile but also semi-volatile and difficulty-volatile substances and the range of synthetic ingredients can embrace representatives from almost all classes of substances, as will be evident from the following compilation:

Natural products such as angelica seed oil, tree moss absolute, bergamot oil, cardamom oil, acetylated cedarwood oil (e.g. Vertofix ® IFF or Cedartone ® Givaudan), oak moss, pine-needle oil, galbanum oil, geranium oil, jasmine absolute and its substitute, lavender oil, lavandin oil, patchouli oil, petitgrain oil (Paraguay), sandalwood oil, vetiver oil, ylang-ylang oil and lemon oil.

Alcohols such as cis-6-nonenol, linalool, citronellol, geraniol, natural rhodinol, α-terpineol, phenylethyl alcohol, phenylpropyl alcohol and cinnamic alcohol.

Aldehydes such as 2,6-dimethyl-5-heptanal, decanal, methylnonylacetaldehyde, hydroxycitronellal, α-amylcinnamaldehyde, cyclamen aldehyde and p-tert. butyl- α-methyl-dihydro-cinnamaldehyde (e.g. Lilial ® Givaudan).

Ketones such as α-ionone, acetylcedrene and p-methyl-acetophenone.

Esters such as cis-3-hexenyl acetate, cis-3-hexenyl benzoate, ethyl acetoacetate, linalyl acetate, geranyl acetate, terpenyl acetate, phenylethyl acetate, styrallyl acetate, p-tert.butyl-cyclohexyl acetate, 4-[4-methyl-2-pentenyl]-cyclohex-3-en-1-yl-carbinyl acetate (e.g. Myraldyl acetate ® Givaudan), cinnamyl formate, benzyl acetate, benzyl salicylate and amyl salicylate.

Lactones such as γ-undecalactone and coumarin.

Various additional substances frequently used in perfumery such as musk compounds (musk, ambrette, musk ketone, 12-oxa-hexadecanolide e.g. Musc 174 ® Naarden), indole, p-menthane-8-thiol-3-one, eugenol, acetaldehyde propylphenylethyl acetal and methyl 1-methylcyclododecyl ether (e.g. Madrox ® Givaudan).

The effect of freshness and naturalness which can be achieved by adding I to corresponding compositions, particularly those having flowery directions, has proved itself to be especially surprising and valuable. This effect was unexpected having regard to the olfactory outflow of the individual compound (constant flow over 48 hours, especially green-woody, but without a fresh effect). In the case of a substance containing 15 carbon atoms it was much more likely that the opposite effect, namely a certain lasting heavyness, would be encountered.

It is also surprising that I in fruity-green notes, as shown in the following Example 5 (melon), in spite of the individual green character does not underline this green direction, but a nuancing which intensively restores the fruit flesh with its sweetness comes to the forefront.

The compounds of formula I can accordingly be used in odorant compositions in wide limits which, for example, can extend from 0.1% in the case of detergents to 30% in the case of alcoholic solutions. It will, however, be appreciated that these values are not limiting values, since the experienced perfumer can also achieve effects with lower concentrations or can formulate novel complexes with higher concentrations. The preferred concentrations vary between 0.5% and 25%. The odorant compositions prepared with I can be used for all kinds of perfumed goods (e.g. Eau de Cologne, eau de toilette, extracts, lotions, creams, shampoos, soaps, salves, powders, toothpastes, mouth washes, deodorants, detergents, tobacco etc). In particular, the use of compositions containing I in soaps and detergents produces a very desirable effect. Thus, by adding I to the composition of Example 3 hereinafter the odour of soap perfumes in this manner (1.2%) is considered to be very much fresher and more flowery in spite of the addition of the woody-green-fatty compound I. This note also lasts over a longer period.

A washing powder having the following composition:

| | |
|---|---|
| Anion-active washing substance | 6% |
| Non-ionic washing substance | 5% |
| Soap powder | 7% |
| Sodium tripolyphosphate | 38% |
| Sodium silicate | 7% |
| Carboxymethylcellulose | 1% |
| Water | 3% |
| Sodium sulphate | 38% | is likewise very much stronger in its flowery-green olfactory note after the addition of, for example, 0.1%–0.5%, especially 0.2%, of the odorant composition of Example 3. Washing trials undertaken therewith show, compared with washing powder perfumed without the addition of I, a surprising result: not only in the case of hand washing (30° C.) but also in the case of machine washing (60° C.) the superiority of the composition containing I shows itself in that this is strongly imparted to textiles washed therewith. The compounds of formula I are accordingly surprisingly characterised not only by pure perfumistic effects, but also by the capability of acting substantively themselves and also of retaining this effect in combination with other odorant substances and at the same time of allowing the corresponding odorant substance mixtures to act substantively.

The following Examples illustrate the present invention:

EXAMPLE 1

120 g (0.79 mol) of cis-4-caranone are placed in a three-necked flask provided with a stirrer, a dropping funnel and a thermometer and cooled to 0° C. 110 g (1.67 mol) of powdered 85% potassium hydroxide are added while stirring so that the temperature does not rise above 35° C. After completion of the addition, the mixture is stirred for a further 1 hour at 0° C. 84 g (0.8 mol) of prenyl chloride are then added dropwise so that the temperature again rises to at most 35° C. After stirring at room temperature for 12 hours, the mixture is poured on to ice, exhaustively extracted with diethyl ether, the combined ether extracts are washed neutral with water, dried over sodium sulphate and subsequently freed from solvent. The crude product is fractionally distilled over a 50 cm packed column in vacuo (oil pump) and thus yields 60.5 g of olfactorily good material of boiling point 93° C./0.2 mmHg; $n_D^{20} = 1.4841$. A main product as well as a byproduct eluted before and a byproduct eluted after this can be recognised in the gas chromatogram. The product mixture has the approximate composition 11% (A), 83% (B) and 6% (C).

The isomers can be produced in practically pure form (above 95%) by preparative gas chromatography and have the following spectral properties:

A: IR: 1700, 1452, 1376, 1205–1235 (broad), 1158, 1110, 1082, 1048, 1012, 986, 962, 830 cm$^{-1}$.

NMR: 0.64 (m, 1H); 0.92 (m, 1H); 0.96 (s, 3H); 0.98 (d, J=7, 3H); 1.06 (s, 3H); 1.20 (m, 1H); 1.62+1.73 (each s, each 3H); 2.0–2.5 (m, 5H); 5.1 (m, 1H) δppm.

MS: 220(11,M+), 151(12), 137(9), 123(18), 109(21), 95(28), 91(26), 79(27), 77(26), 69(30), 67(29), 55(29), 53(30), 41(100).

B: IR: 1698, 1452, 1408, 1376, 1348, 1292, 1205–1232 (broad) 1156, 1132, 1120, 1108, 1086, 1048, 1014, 990, 964, 896, 858 cm$^{-1}$.

NMR: 0.63–1.2 (m below s, 2H); 0.88 (s, 3H); 0.91 (s, 3H); 1.07 (s, 3H); 1.68+1.73 (each s, 6H); 2.03 (m, 1H); 2.28–2.52 (m, 4H); 5.02 (t, J=7 1H) δppm.

MS: 220(8,M+), 205(9), 151(25), 137(26), 123(100), 109(78), 95(32), 81(37), 69(56), 55(20), 53(19), 41(68).

C: IR: 1670, 1448, 1378, 1354, 1322, 1282, 1205–1235 (broad), 1116, 1082, 1040, 1012, 980, 910, 880 cm$^{-1}$.

NMR: 0.84–1.24 (m below d and s, 2H); 0.95 (d, J=6, 3H); 1.16 (s, 6H); 1.36–1.53 (m, 2H); 1.66 (2 converging s, 6H); 1.78–2.52 (m, 4H); 5.00 (t, J=6, 1H) δppm.

MS: 220(11,M+), 205(7), 152(47), 137(54), 123(24), 109(98), 95(74), 82(31), 69(100), 55(33), 53(29), 41(92).

The main component B is identified unequivocally as 3,7,7-trimethyl-3-(3'-methyl-2'-butenyl)-bicyclo[4.1.0]-heptan-4-one by the $^{13}$C-NMR-spectrum on the basis of the singlets at 19.3 ppm (as in the cis-4-caranone) and 46.12 ppm (new).

On the other hand, the two components A and C have already in the $^1$H-NMR-spectrum the characteristic doublet of the secondary methyl group, which is also observable in the cis-4-caranone, and are accordingly the isomeric 3,7,7-trimethyl-5-(3'-methyl-2'-butenyl)-bicyclo[4.1.0]-hetpan-4-ones.

EXAMPLE 2

30 ml of dimethoxymethane, previously purified over basic aluminium oxide, are placed in a 200 ml four-necked flask provided with a stirrer, two dropping funnels, a thermometer and a reflux condenser. 15 g (0.23 mol) of powdered 85% potassium hydroxide are subsequently introduced while stirring and the entire content of the flask is cooled to 0° C. At this temperature there are thereupon simultaneously added drop-wise from two dropping funnels 11.4 g (0.075 mol) of cis-4-caranone and 7.8 g (0.0746 mol) of prenyl chloride within 2 hours so that the temperature does not rise above +2° C. The mixture is stirred at room temperature for a further 2 hours, then poured on to ice and exhaustively extracted with diethyl ether. The organic phase is washed neutral with water, dried over sodium sulphate and the solvent mixture is removed in a rotary evaporator at 30° C./20 mmHg. The crude product (14.6 g) is fractionally distilled over a short Widmer column under a high vacuum. After a fore-run of 4.1 g of cis-4-caronone, I (7.6 g) can be distilled at 77° C./0.05 mmHg ($n_D^{20} = 1.4865$). The product obtained is an isomer mixture of 85% Ia (B of Example 1) and 15% Ib (A of Example 1).

In the following Examples "I" denotes the isomer mixture of Ia/Ib obtained in Examples 1 and 2.

EXAMPLE 3

| Flowery base | Parts by weight |
| --- | --- |
| Propyleneglycol | 200 |
| Benzyl acetate | 100 |
| α-Ionone | 100 |
| α-Amylcinnamaldehyde (substitute) | 100 |
| Citronellol | 50 |
| p-Tert. butylcyclohexyl acetate | 50 |
| Linalool | 50 |
| Methyl 1-methylcyclododecyl ether | 50 |
| Benzyl salicylate | 30 |
| Vertofix ® (IFF) | 30 |
| Eugenol | 30 |
| Cedartone ® (acetylcedrene) | 30 |
| Styrallyl acetate | 20 |
| Terpenyl acetate | 20 |
| Musc 174 ® (Naarden) | 20 |
| Geraniol | 20 |
| Linalyl acetate | 20 |
| Ylang-ylang oil | 10 |
| Acetaldehyde propylphenylethyl acetal | 10 |
| Hydroxycitronellal | 5 |
| Methylnonylacetaldehyde (10% in ethyl phthalate) | 5 |
| | 950 |

If 50 parts of I are added to this flowery composition, which is in the direction of hyacinth, then it becomes much more rounded-off, softer, more flowery and fresher. The ionone note is very pleasantly enveloped. In the bottom a freesia note surprisingly arises from the hyacinth. The powdery-woody note which appears in the original base is masked by the flowery note. The fresh note lasts over a period of 24 hours.

EXAMPLE 4

| Flowery composition in the direction of lilac | |
| --- | --- |
| | Parts by weight |
| Terpineol | 260 |
| Hydroxycitronellal | 200 |
| Phenylethyl alcohol | 160 |
| Cinnamic alcohol (substitute) | 100 |
| Phenylpropyl alcohol | 100 |
| Cinnamyl formate | 20 |
| Geranyl acetate | 10 |
| Musk ketone | 10 |
| Jasmine (substitute) | 10 |
| Eugenol | 5 |
| Indole (10% in ethyl alcohol) | 5 |
| p-Menthane-8-thiol-3-one (10% in propyleneglycol) | 5 |
| p-Methylacetophenone | 5 |
| C-10 aldehyde (10% in propyleneglycol) | 5 |
| δ-Undecalactone | 5 |
| | 900 |

This base, prepared exclusively from synthetic substances, leaves behind the impression of a still very synthetic-chemical lilac. After the addition of 100 parts of I to this base, the resulting base has an extraordinary natural note and is now reminiscent of fresh flowering lilac.

EXAMPLE 5

| Fruity perfume base in the direction of melon | |
| --- | --- |
| | Parts by weight |
| Propyleneglycol | 180 |
| Linalyl acetate | 120 |
| Myraldyl acetate ® (Givaudan) | 120 |
| Hexenyl benzoate | 100 |
| Cyclamen aldehyde | 80 |
| 2,6-Dimethyl-5-heptenal (10% in ethyl alcohol) | 60 |
| Ethyl acetoacetate | 60 |
| Cis-6-nonenol (10% in ethyl alcohol) | 40 |
| Lilial ® (Givaudan) | 20 |
| Hexenyl acetate (10% in alcohol) | 20 |
| | 800 |

If 200 parts of I are added to this fruity base, then there results from the original fruity-green melon, which has a basic note reminiscent of melon skin, a much sweeter and rounded-off melon note. The fruit flesh note is pleasantly underlined.

EXAMPLE 6

| Chypre base in the direction of mens Cologne | |
| --- | --- |
| | Parts by weight |
| Propyleneglycol | 200 |
| Bergamot oil | 100 |
| Methyl 1-methylcyclododecyl ether | 100 |
| Hydroxycitronellal | 80 |
| Musc 174 ® (Naarden) | 60 |
| Patchouli oil | 50 |
| Pine needle oil | 50 |
| Citronellol | 40 |
| Tree moss absolute (50% in propyleneglycol) | 30 |
| Galbanum oil | 30 |

-continued

| Chypre base in the direction of mens Cologne | |
|---|---|
| | Parts by weight |
| Lemon oil | 20 |
| Petitgrain oil (Paraguay) | 20 |
| Cedartone ® (IFF) | 20 |
| Cardamom oil | 5 |
| Angelica seed oil | 5 |
| α-Ionone | 40 |
| Linalool | 50 |
| | 900 |

If 100 parts of I are added to this base, which can be used for mens Cologne directions, then the thus-obtained base is much lighter, more flowery and softer. I very advantageously envelops the harsh, prominent galbanum note of the original composition and forms, together with the ionone-musk note, a novel complex.

EXAMPLE 7

| Perfume composition in the direction of Fougerè | |
|---|---|
| | Parts by weight |
| Lavender oil | 200 |
| Amyl salicylate | 200 |
| Coumarin | 100 |
| Oak moss absolute (Yugoslavian) | 80 |
| Geranium oil (Bourbon) | 60 |
| Bergamot oil | 60 |
| Musk ambrette | 60 |
| Petitgrain oil (Paraguay) | 40 |
| α-Ionone | 40 |
| Vetiver oil (Bourbon) | 40 |
| Sandalwood oil | 40 |
| Patchouli oil | 20 |
| α-Amylcinnamaldehyde (substitute) | 20 |
| Eugenol | 20 |
| | 980 |

If 20 parts of I are added to this Fougerè base, then the oak moss note recedes in the novel composition. The addition confers more softness to the novel base. Moreover, the lavender note is very pleasantly underlined, and this results in the novel composition having a substantially fresher impression.

EXAMPLE 8

| Perfume base in the direction of rose | |
|---|---|
| | Parts by weight |
| Phenylethyl alcohol | 400 |
| Citronellol | 180 |
| Geraniol | 150 |
| Linalool | 100 |
| α-Ionone | 50 |
| Hydroxycitronellal | 50 |
| Phenylethyl acetate | 30 |

-continued

| Perfume base in the direction of rose | |
|---|---|
| | Parts by weight |
| Benzyl acetate | 20 |
| | 980 |

If 20 parts of I are added to this conventional rose base, then the rosy character is substantially altered; whereas the original base corresponds to a red rose, a yellow rose is generated by the addition.

EXAMPLE 9

| Perfume base in the direction of lily of the valley | |
|---|---|
| | Parts by weight |
| Hydroxycitronellal | 430 |
| Rhodinol extra | 350 |
| Linalool | 80 |
| α-Amylcinnamaldehyde | 50 |
| Sandalwood oil | 50 |
| Ylang-ylang oil | 20 |
| | 980 |

If 20 parts of I are added to this lily of the valley base, then the typical fresh-green character of this flower is brought to the forefront. I confers much more naturalness to the base.

I claim:

1. A composition consisting of compounds of the general formula:

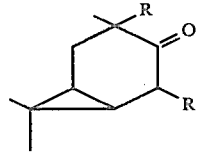

wherein one of the R symbols represents a 3-methyl-2-butenyl group and the other represents a hydrogen atom.

2. A composition according to claim 1 which is about 80% to 90% 3,7,7-trimethyl-3-(3'-methyl-2'-butenyl)-bicyclo[4.1.0]-heptan-4-one and about 20% to 10%, 3,7,7-trimethyl-5-(3'-methyl-2'butenyl)-bicyclo[4.1.0]-hetpan-4-one.

3. A composition according to claim 2 which is between 85% 3,7,7-trimethyl-3-(3'methyl-2'-butenyl)-bicyclo[4.1.0]-heptan-4-one and between 15% 3,7,7-trimethyl-5-(3'-methyl-2'-butenyl)-bicyclo[4.1.0]-heptan-4-one.

4. A composition of claim 1 consisting essentially of 3,7,7-trimethyl-3-(3'methyl-2'-butenyl)-bicyclo-[4.1.0]-heptan-4-one.

5. A composition of claim 1 consisting essentially of 3,7,7-trimethyl-5-(3'methyl-2'-butenyl)-bicyclo-[4.1.0]-heptan-4-one.

* * * * *